United States Patent [19]
Thornfeldt

[11] Patent Number: 5,326,790
[45] Date of Patent: Jul. 5, 1994

[54] ADMINISTRATION OF SKIN MEDICATIONS BY USE OF DICARBOXYLIC ACIDS AND DERIVATIVES

[75] Inventor: Carl R. Thornfeldt, Ontario, Oreg.

[73] Assignee: Dermatologic Research Corporation, Napa, Calif.

[21] Appl. No.: 869,920

[22] Filed: Apr. 16, 1992

Related U.S. Application Data

[60] Continuation-in-part of Ser. No. 324,997, Mar. 15, 1989, abandoned, which is a division of Ser. No. 164,317, Mar. 4, 1988, abandoned, which is a continuation-in-part of Ser. No. 932,954, Nov. 19, 1986, abandoned.

[51] Int. Cl.$^5$ .................. A01N 37/02; A01N 25/00
[52] U.S. Cl. .................. 514/784; 514/946; 514/947; 514/785; 514/547
[58] Field of Search ............ 514/784, 785, 947, 547

[56] References Cited

FOREIGN PATENT DOCUMENTS

| | | |
|---|---|---|
| 5167245 | 12/1980 | Japan . |
| 2150433 | 7/1985 | United Kingdom . |
| WO/01000 | 3/1983 | World Int. Prop. O. . |

*Primary Examiner*—Paul J. Killos
*Attorney, Agent, or Firm*—Townsend and Townsend Khourie and Crew

[57] ABSTRACT

The topical administration of therapeutic agents to a variety of disease conditions, both cutaneous and systemic, is enhanced by combining the therapeutic agents with dicarboxylic acids or analogs of such acids, which include mono- and dimercapto derivatives, salts, esters, amides and anhydrides. Preferred dicarboxylic acids are azelaic and dodecanedioic acids and their monoglyceride and sucrose salts. Preferred therapeutic agents are antiinflammatory compounds, antihistamine compounds, antineoplastic compounds, vitamin D and retinoid agents. Specific examples of some of these compounds are 5-fluorouracil, methotrexate, bleomycin, carmustine and nitrogen mustard. The acids and analogs of this invention enhance the penetration capabilities of the therapeutic agents and are thus effective in promoting the therapeutic effect of these agents inside diseased cells, particularly for diseases such as inflammatory skin diseases and premalignant and non-melanoma malignant skin tumors.

14 Claims, No Drawings

ADMINISTRATION OF SKIN MEDICATIONS BY USE OF DICARBOXYLIC ACIDS AND DERIVATIVES

CROSS-REFERENCE TO RELATED APPLICATIONS

This application is a continuation-in-part of co-pending application Ser. No. 07/324,997, filed Mar. 15, 1989, now abandoned which is a division of application Ser. No. 07/164,317, filed Mar. 4, 1988, now abandoned, which is continuation-in-part of copending application Ser. No. 06/932,954, filed Nov. 19, 1986, now abandoned.

BACKGROUND AND SUMMARY OF THE INVENTION

This invention relates to the treatment of skin conditions such as inflammatory skin diseases and various kinds of skin tumors by the topical administration of medicaments. In accordance with this invention, it has been discovered that certain dicarboxylic acids and derivatives of these acids are capable of carrying therapeutically active agents into diseased cells where these agents can control, inhibit or eliminate the abnormal cell processes responsible for the disease condition. These dicarboxylic acids and acid analogs not only enhance the degree to which the therapeutic agents penetrate the cells to reach the regions of interest, but also suppress the overall toxicity of the agents, decreasing or eliminating the damage which they would otherwise do to the living organism and its normal cells. The dicarboxylic acids and acid analogs enhance penetration of medications across the cell wall and stratum corneum, reduce the occurrence of cell and skin injury by the medications, and potentiate the therapeutic activity of the agents. The acids and analogs are thus useful as carriers of the therapeutic agents which are otherwise poorly penetrating or which otherwise have undesirable toxic side-effects en route to sites where the agents can have a valuable therapeutic effect. Included among the derivatives of the acids are mono- and dimercapto derivatives, salts, esters, amides and anhydrides. Still further penetrating ability can be achieved by combining the acids and acid derivatives with stratum corneum penetrants in a topical application.

DETAILED DESCRIPTION OF THE INVENTION

Dicarboxylic acids of primary interest in accordance with this invention are those having 7 to 13 carbon atoms, with those having 8 to 12 carbon atoms preferred. This includes both straight-chain and branched-chain compounds, both saturated and unsaturated (i.e., having one or more double bonds). Examples are pimelic (1,7-heptanedioic) acid, suberic (1,8-octanedioic) acid, azelaic (1,9-nonanedioic) acid, sebacic (1,10-decanedioic) acid, and 1,12-dodecanedioic. Azelaic and dodecanedioic acids are of particular interest.

Analogs of dicarboxylic acids within the scope of the present invention include mono- and dimercapto derivatives (in which the —OH is replaced by —SH), salts (particularly alkali and alkaline earth metal salts such as, for example, sodium or potassium), esters, amides and anhydrides. Included among the esters are mono- and dialkyl esters and mono- and diesters prepared from polyols and oligo- and polysaccharides. Examples of such polyols are glycerol, polyethylene glycol and polypropylene glycol, and examples of oligo- and polysaccharides are sucrose, lactose and starch. Preferred esters are monoglycerides and sucrose esters.

Therapeutic agents which will benefit from the use of these dicarboxylic acids include a wide range of agents, both prescription and non-prescription. The following are examples of classes of such agents:

antiinflammatory agents including corticosteroids, sulfones, colchicine, sulfasalazine, chloroxine, selenium, sulfide and zinc pyrithione antibacterial agents including quinolones, macrolide, penicillin, cephalosporin, sulfonamide, and tetracyclines antineoplastic agents including methotrexate, piritrexim, cis-platinin, 5-fluorouracil, bleomycin, carmustine, hydroxyurea, azathioprine and nitrogen mustard antivirals including acyclovir, idoxuridine, zidovudine, ddI, vidarabine, and trifluridine antifungals including ketoconazole, econazole, miconazole, clotrimazole, cicloprix, tolnaftate, and griseofulvin antihistamines including diphenhydramine, astemizole, hydroxyzine, doxepin, amitriptyline, cyproheptadine, and sodium cromolyn antipruritics including camphor, menthol, phenol, benzocaine, benzyl alcohol, salicylic acid, dyclonine and pramoxine carboxylic acid analogs including 1-monolaurin natural and synthetic vitamins and derivatives including vitamin D and its analogs, and retinoids artemisinin analogs including dihydroartemisinin propyl carbonate, artemether, artesunate, arteether, and artelinic acid This invention is of particular interest in connection with the administration of antiinflammatories, antineoplastics, antihistamines, vitamin D analogs and retiniod agents.

Types of diseases and disease states to which the invention may be applied with effective results are many and varied. Included among these are skin and systemic diseases, including many viral, bacterial and fungal diseases, as well as malignant and premalignant conditions and other inflammatory diseases, such as various types of arthritis. Examples are papulosquamous diseases, eczematous diseases, ichthyotic diseases, infectious diseases in general, actinic keratoses, seborrheic dermatoses, Bowen's disease, cutaneous T cell lymphomas, warts, condyloma or molluscum contagiosa, and basal cell and squamous cell carcinomas. The invention is particularly effective in the treatment of inflammatory skin diseases and premalignant and non-melanoma malignant skin tumors.

The effectiveness of therapeutic formulations which include the dicarboxylic acid and acid derivatives of this invention is in certain cases enhanced by the inclusion in the formulation of stratum corneum penetration enhancers and/or keratolytics. The nature, composition and concentration of these additives is not critical and may vary widely. Optimal selection of the agent and its concentration will be within the routine skill of those skilled in the art. Examples of such additives are:

salicylic acid
laureth-4
isopropyl palmitate
propylene glycol
oleic acid
ethyl alcohol isopropyl alcohol
oleyl alcohol
N-methyl-2-pyrrolidone
sulfur
dimethylacetamide
diethylamide
dimethylformamide
dimethyl sulfoxide
AZONE (available from Nelson Research Laboratories, Irvine, Calif.)
transretionic acid (available from Ortho Pharmaceuticals, Raritan, N.J.).

The formulations described above may be administered topically, and will generally be applied to skin and/or mucous membranes. The formulations may be in the form of any of the various known mixtures and combinations which will permit even spreading of the active ingredient over the infected area. Examples include creams, emollient creams, lotions, solutions, ointments, unguents, shampoos, aerosols, gels and pastes.

Additional inactive ingredients may be included to place the formulations in a cosmetically acceptable form or to facilitate their administration. These additional ingredients may include surfactants, humectants, wetting agents, emulsifiers or propellants that permit even spreading over the affected area. Further additives include oils, fats, waxes, alcohol, stabilizers, preservatives, dyes, fragrances and conditioners.

The therapeutic agent and the entire formulation itself will be administered in therapeutically effective amounts in the practice of this invention. The term "therapeutically effective amount" is used herein to denote any amount which will produce a substantial improvement in a disease condition when applied to the affected area repeatedly over a period of time. The amount will vary with the condition being treated, the stage of advancement of the condition, and the type and concentration of the formulation applied. Appropriate amounts in any given instance will be readily apparent to those skilled in the art or capable of determination by routine experimentation.

The concentration of the therapeutic agent can likewise vary widely, for the same reasons. In most applications, the concentration of the therapeutic agent will range from about 0.01% to about 40% by weight, and preferably from about 0.1% to about 10% by weight.

The dicarboxylic acid or acid analog will also be administered in a therapeutically effective amount. The term "therapeutically effective amount" when used to describe the dicarboxylic acid or acid analog denotes an amount which will enhance the penetration of the therapeutic agent into the skin or cells where the activity of the therapeutic agent is needed. As in the case of the therapeutic agent, the therapeutically effective amount of the dicarboxylic acid or acid analog is most conveniently expressed in terms of the weight percent of the acid or acid analog. This will vary as well, with preferred ranges in weight percent being the same as those of the therapeutic agent. The ratio of the dicarboxylic acid to the therapeutic agent will generally range from about 0.05:1 to about 50:1, and preferably from about 0.5:1 to about 5:1.

The formulation itself is applied in the same manner as any topical formulation, generally with repeated applications on an hourly or daily basis, depending on the condition being treated, until clearance of the condition is achieved.

The following example is offered strictly for purposes of illustration, and is intended neither to limit nor define the invention in any manner.

EXAMPLE

A topical formulation was prepared as follows:
One pound of Cetaphil cream and 90 grams of azelaic acid were heated separately until each was liquified (approximately two hours). Cetaphil cream is a commercially available non-prescription mixture of water, ethyl alcohol, propylene alcohol, sodium lauryl sulfate, stearyl alcohol, methylparaben, propylparaben and butylparaben obtainable from Owen Laboratories, San Antonio, Tex. Once the cream and acid were liquified, the acid was slowly beat into the cream to form a smooth homogeneous cream. The resulting cream was then combined with an equal amount of 5% 5-fluorouracil cream (Efudex, obtained from Roche Laboratories, Nutley, N.J.).

Four patients with multiple sun-induced premalignant growths on the backs of hands were treated twice daily with the above formulation for ten weeks. During this time, more than 80% of the lesions on the treated hands resolved. The treatment was accompanied by only mild inflammation.

The foregoing description is offered primarily for purposes of illustration. It will be readily apparent to those skilled in the art that numerous variations in both the formulations and their method of use, not mentioned above, may be made without departing from the spirit and scope of the invention.

What is claimed is:

1. A method for administering a therapeutic agent to a subject suffering from a disease controllable thereby, said method comprising administering to said subject a composition comprising:
   (a) a therapeutically effective amount of said therapeutic agent, and
   (b) a therapeutically effective of a compound selected from the group consisting of dicarboxylic acids having 7 to 13 carbon atoms, and mono- and dimercapto derivatives, salts, monoglyceride esters, sucrose esters, amides and anhydrides thereof.

2. A method in accordance with claim 1 in which said compound is a member selected from the group consisting of dicarboxylic acids having 8 to 12 carbon atoms, and mono- and dimercapto derivatives, salts, monoglyceride esters, sucrose esters, amides and anhydrides thereof.

3. A method in accordance with claim 1 in which said compound is a member selected from the group consisting of azelaic and dodecanedioic acids, and mono-and dimercapto derivatives, salts, monoglyceride esters, sucrose esters, amides and anhydrides thereof.

4. A method in accordance with claim 1 in which said compound is a member selected from the group consisting of azelaic and dodecanedioic acids, and salts, monoglyceride esters and sucrose esters thereof.

5. A method in accordance with claim 1 in which said compound is a member selected from the group consisting of azelaic acid, salts of azelaic acid, and monoglyceride and sucrose esters of azelaic acid.

6. A method in accordance with claim 1 in which said compound is a member selected from the group consisting of dodecanedioic acid, salts of dodecanedioic acid, and monoglyceride and sucrose esters of dodecanedioic acid.

7. A method in accordance with claim 1 in which said compound is a member selected from the group consisting of azelaic and dodecanedioic acids.

8. A method in accordance with claim 1 in which said therapeutic agent is a member selected from the group consisting of antiinflammatory compounds, antimicrobial compounds, antineoplastic compounds, antipruritic compounds, carboxylic acid analogs, natural and synthetic vitamins and vitamin derivatives, and artemisinin analogs.

9. A method in accordance with claim 1 in which said therapeutic agent is a member selected from the group consisting of antiinflammatory compounds, antihistamine compounds, antineoplastic compounds, vitamin D analogs and retinoids.

10. A method in accordance with claim 1 in which said therapeutic agent is a member selected from the group consisting of 5-fluorouracil, methotrexate, bleomycin, carmustine and nitrogen mustard.

11. A method in accordance with claim 1 in which said compound is a member selected from the group consisting of azelaic and dodecanedioic acids, and salts, monoglyceride esters and sucrose esters thereof, and said therapeutic agent is a member selected from the group consisting of 5-fluorouracil, methotrexate, bleomycin, carmustine and nitrogen mustard.

12. A method for administering a therapeutic agent to a subject suffering from a disease controllable thereby, said method comprising administering to said subject a composition comprising:
   (a) a therapeutically effective amount of said therapeutic agent, and
   (b) a therapeutically effective of a compound selected from the group consisting of dicarboxylic acids having 7 to 13 carbon atoms, and mono- and dimercapto derivatives and salts thereof.

13. A method for administering a therapeutic agent to a subject suffering from a disease controllable thereby, said method comprising administering to said subject a composition comprising:
   (a) a therapeutically effective amount of said therapeutic agent, and
   (b) a therapeutically effective of a compound selected from the group consisting of dicarboxylic acids having 7 to 13 carbon atoms, and salts thereof.

14. A method for administering a therapeutic agent to a subject suffering from a disease controllable thereby, said method comprising administering to said subject a composition comprising:
   (a) a therapeutically effective amount of said therapeutic agent, and
   (b) a therapeutically effective of a compound selected from the group consisting of dicarboxylic acids having 7 to 13 carbon atoms.

* * * * *

UNITED STATES PATENT AND TRADEMARK OFFICE
CERTIFICATE OF CORRECTION

PATENT NO. : 5,326,790

DATED : July 5, 1994

INVENTOR(S) : Carl R. Thornfeldt

It is certified that error appears in the above-indentified patent and that said Letters Patent is hereby corrected as shown below:

Column 3, line 11, "transretionic" should read --transretinoic--.

Signed and Sealed this

First Day of November, 1994

Attest:

BRUCE LEHMAN

Attesting Officer

Commissioner of Patents and Trademarks